United States Patent [19]

Young et al.

[11] Patent Number: 4,668,632
[45] Date of Patent: May 26, 1987

[54] SPARGER AND APPARATUS FOR AND METHOD OF GROWING CELLS

[75] Inventors: Michael W. Young, Kennebunkport; Henry W. Founds, Scarborough, both of Me.; Peter Zuk, Jr., Harvard, Mass.

[73] Assignee: VXR, Inc., Portland, Me.

[21] Appl. No.: 698,654

[22] Filed: Feb. 6, 1985

[51] Int. Cl.[4] .................. C12M 3/00; B01D 47/02
[52] U.S. Cl. ............................. 435/284; 435/313; 435/285; 210/220; 261/124; 261/121.1
[58] Field of Search ................... 435/284–286, 435/313–315, 813, 818; 435/240, 241; 210/220; 261/121 R, 124

[56] References Cited

U.S. PATENT DOCUMENTS

| | | | |
|---|---|---|---|
| 2,207,768 | 7/1940 | Weijlard et al. | 435/313 X |
| 2,305,796 | 12/1942 | Seidel | 435/313 X |
| 3,275,528 | 9/1966 | Ainis | 435/284 X |
| 3,732,148 | 5/1973 | Franckowiak et al. | 435/813 X |
| 3,790,141 | 2/1974 | Champeau | 261/177 |
| 3,880,716 | 4/1975 | Engelbart et al. | 195/108 |
| 3,963,581 | 6/1976 | Giacobbe et al. | 195/142 |
| 3,970,731 | 7/1976 | Oksman | 261/122 |
| 3,978,176 | 8/1976 | Voegeli | 261/122 |
| 4,173,516 | 11/1979 | Katinger et al. | 435/286 |
| 4,183,787 | 1/1980 | Roesler et al. | 435/43 |
| 4,201,691 | 5/1980 | Asher et al. | 261/124 X |
| 4,201,845 | 5/1980 | Feder et al. | 435/285 |
| 4,225,671 | 9/1980 | Puchinger et al. | 435/285 X |
| 4,308,351 | 12/1981 | Leighton et al. | 435/284 |
| 4,557,879 | 12/1985 | Weber | 261/124 X |

FOREIGN PATENT DOCUMENTS

| | | |
|---|---|---|
| 0052252 | 11/1980 | European Pat. Off. |
| 1247395 | 6/1969 | United Kingdom |
| 1441229 | 12/1974 | United Kingdom |
| 1572624 | 4/1977 | United Kingdom |

Primary Examiner—Larry Jones
Attorney, Agent, or Firm—David G. Conlin; Linda M. Buckley

[57] ABSTRACT

A sparger useful for introducing gas into a liquid is composed of one or more gas-permeable members positioned between a gas inlet means and a gas distribution means. A method and apparatus for culturing cells, eukaryotic cells and hybridomas in particular, wherein circulation of a liquid medium contained in the apparatus is achieved by gas introduced into the liquid medium by means of the aforementioned sparger.

35 Claims, 15 Drawing Figures

SPARGER AND APPARATUS FOR AND METHOD OF GROWING CELLS

FIELD OF THE INVENTION

This invention relates to a device for introducing gas into a liquid contained in a vessel, hereinafter sometimes referred to as a sparger, and more particularly to a unique sparger for use in methods of an apparatus for cultivating living cells, especially eukaryotic cells and hybridomas.

BACKGROUND OF THE INVENTION

Spargers comprising perforated plates made of non-porous materials such as ceramic or stainless steel have been used to introduce a gas in the form of bubbles into a liquid for the purpose of providing oxygen, carbon dioxide or some other gas or combination of gases to the liquid. Such spargers have a limited range of pore sizes and consequently bubble size and are relatively expensive to manufacture. Other spargers known in the art are made from materials such as sintered open-pore plastics, resin matrices enclosing spherical particles of substantially uniform size and sintered powdered metals. Due to the nature of the materials comprising these spargers it is difficult to achieve uniform bubbling and to control the size of bubbles. This lack of control may have an adverse effect upon the liquid being aerated or on biological material contained therein. For example, larger bubbles have greater shear force and may damage fragile cells in the liquid or, if the liquid is blood, cause clotting. Spargers comprised of metals may react with the liquid medium or be toxic to cells contained therein.

The sparger of the present invention represents an improvement over the prior art in that it is free of the foregoing disadvantages and inexpensive to manufacture. The material through which the gas is passed to form bubbles produces uniform bubbling and the pore size of the material is selected from a wide range to produce bubbles of the desired size. This invention represents a further improvement in that the bubbles are released into the medium in such a way as to minimize coalescing of the bubbles.

Although the sparger of the present invention may be used in any process where gas is injected into a liquid it has particular application in the field of biotechnology for the culturing of living cells, e.g., in fermentation and especially in the cultivation of eukaryotic cells such as hybridomas.

All living cells must be provided with a suitable environment in which to grow and an adequate supply of oxygen and nutrients to grow. A liquid growth medium provides for the nutritional requirements of living cells. In order to make the nutrients and oxygen available to the cells, the medium must be thoroughly mixed.

A variety of techniques and apparatus has been developed to grow cells, the simplest of which involve roller bottles containing cells and medium. The cells attach to the inside surface of the roller bottle and the bottle is rotated to provide alternate, constant bathing of the cells with liquid medium and exposure to air. The operation of more sophisticated apparatus typically involves introducing gas into the system to provide the oxygen needed for aerobic growth and circulation of the medium by internal or external mechanical means to make the nutrients in the medium and introduced gas available to the cells. The velocity at which the liquid medium circulates has an effect on cell growth. A high velocity of circulation physically stresses the cells and may damage or destroy certain types of cells. Cells of higher eukaryotes are very suceptible to damage of this type.

The circulation of the medium may be imparted in certain cell culture apparatus by introducing gas into a culture vessel in such a manner to cause circulation of the liquid medium contained therein. A vessel in which circulation of the medium is achieved in this manner typically is provided with one or more baffles separating the vessel into two or more zones through which the medium may circulate. The circulation of the medium is achieved by introducing a gas in the form of bubbles to modify the density of the liquid, i.e. reducing the density, so that the liquid will rise in the zone in which gas enters and descend in another region after losing some of the injected gas. See e.g. U.S. Pat. Nos. 3,963,581 and 4,183,787, 3,790,141 and 3,880,716. Spargers of various designs have been found useful to introduce gas into a liquid in order to impart a circulatory motion to the liquid. However, most such spargers are not useful for the cultivation of highly sensitive biological materials and particularly eukaryotic cells. Equipment designed to impart a circulatory motion to medium in the cultivation of mammalian cells has utilized perforated plates. See. U.S. Pat. No. 4,173,516.

To avoid or minimize contamination, most cell culturing apparatus use sterile techniques. The medium and the culture vessel are sterilized and a pure culture consisting of a particular living cell is introduced. In order to avoid subsequent contamination, all materials entering the system, including the large amount of oxygen required for aerobic cell culture, are sterilized. The apparatus must be designed so that contamination may be avoided during operation.

Apparatus for growing cells may be designed for batch processing or for a constant flow, steady-state processing.

In batch processing, the culture apparatus is filled with the medium and cells to be grown and growth takes place over a period of time. During this period nutrients and oxygen are supplied to the apparatus and gases produced by the growing cells are removed. However, the cells and materials produced thereby are not removed until culturing is complete.

In constant flow, steady state systems, medium is supplied to and spent medium and product is withdrawn from the reaction vessel continuously and at volumetrically equal rates. Such systems are closer to the growth conditions for mammalian cells, i.e., mammalian cells are constantly surrounded by a circulatory system that supplies nutrients and removes wastes. Some advantages of the continuous flow, steady-state system are greater yields of cell products and ease of production.

The rapidly growing field of biotechnology has provided a means for producing new and improved products by means of genetically engineered microorganisms and fused cells known as hybridomas. The commercial success of industrial applications of recombinant DNA technology and cell fusion techniques, particularly in the pharmaceutical area, will depend upon the successful, large-scale cultivation of eukaryotic cells and hybridomas. However, cultivation of such cells and hybridomas is no simple matter and presents a number of unique problems.

The organisms which have been used most extensively in cell culture have been prokaryotes (e.g. bacteria) or simple eukaryotes (e.g. yeast). These hardy organisms, encased in a tough cell wall, are relatively easy to grow as compared with higher eukaryotic cells which are larger than most microorganisms and enclosed in a delicate plasma membrane. The techniques developed for the growth of microorganisms have limited applicability to the growth of eukaryotic cells because the aforementioned techniques damage these larger, more fragile cells.

Problems with plant cell culture are similar to those of mammalian cells. The type of plant cells that the cellift is best adapted to grow are single plant cells that multiply in suspension, such as algal cells. Additional requirements for growth of plant cells are an adequate medium to provide nutrients for plant cells and a light source for photosynthesis.

Some mammalian cells grow in suspension like microbial cells and most tumor and other transformed cells can be adapted to grow in suspension. However, most higher cells must attach to a solid surface.

Although a variety of methods has been developed to grow mammalian cells both in suspension and attached to a solid surface none has solved the problem of damage described above. The simplest of these techniques is the roller bottle technique previously described herein. There are several immobilization techniques, where non-anchorage dependent ("non-ADC") cells such as hybridomas are fixed to porous ceramic or surfaces of a hollow fiber ultrafilter. Media is then oxygenated (or aerated) and pumped over the immobilized cells. Hybridomas and other cells have been encapsulated in various gelatins or membrane-life capsules for the purpose of increasing cell density, and thereby end product yield. Hybridomas and other non-ADC cells are often grown in spinner culture vessels. This vessel is a simple container with a variety of paddles, turned by a magnetic rotating control. All of the above methods suffer the disadvantage of an insufficiently gentle means to circulate the medium and thus make the nutrients and oxygen available to the cells and, in the case of cells which grow in suspension, to maintain the cells in suspension, without damage to the cells.

Outside of the in vitro systems described above the most popular method is to grow hybridomas in vivo as an ascites tumor in mice. The fluid from the tumor, harvested from the mouse peritoneum, contains the product produced by the hybridoma, i.e., monoclonal antibodies, as well as many other materials produced by the cells of the mouse as a normal by-product of cellular metabolism. Thus, the ascites fluid must be purified to remove these other products. Its use as a human therapeutic is limited both by purification problems and scale of production.

Presently available methods of culturing mammalian cells such as hybridomas are inadequate. Sensitive cells are damaged by currently available methods and such methods do not yield cells in sufficient number or cell product in sufficient quantity. Other methods are limited by purity of products produced and the need for extensive, often difficult purification. Thus, alternative methods for growing eukaryotic cells and hybridomas are currently being sought.

SUMMARY OF THE INVENTION

The present invention provides a device for introducing gas into a liquid which comprises a gas inlet means, at least one gas permeable member disposed adjacent the gas inlet means and gas distribution means disposed adjacent the gas permeable member, the gas inlet means, gas permeable member and gas distribution means being sealably connected.

The present invention also provides a method for introducing gas into a liquid contained in a vessel which comprises the steps of introducing gas into a gas inlet means; passing the gas from the gas inlet means through at least one gas permeable member; and distributing the gas passing from the gas permeable member through a gas distribution means into a liquid medium.

The invention further provides an apparatus and method for cultivating cells, particularly mammalian cells. The apparatus comrprises a container for the liquid medium; at least one baffle means supported within the vessel and spaced from the top and bottom thereof, the baffle means preferably defining at least two regions; a structure for introducing gas into a liquid contained in a vessel so disposed as to introduce gas therethrough comprising a gas inlet means, at least one gas permeable member disposed adjacent to the gas inlet means, and a gas distribution means disposed adjacent to the gas permeable member, the gas inlet means, the gas permeable member and the gas distribution means being sealably connected. The method comprises the steps of introducing gas into a gas inlet means; passing the gas from the gas inlet means through at least one gas permeable member; distributing the gas passing from the gas permeable member through a gas distribution means into a region of the vessel defined by the baffle means so that the gas rises in the region into which it is introduced and falls in another region defined by the baffle means; and continuously circulating the medium thereby. The invention also provides an apparatus for the constant flow steady-state processing of cells. In this embodiment the culture vessel contains an inlet and outlet for the medium.

In order for effective culturing to take place, the gas is introduced so as to cause the medium to circulate over and around the cells, in the case where the cells are grown on a surface, at a rate sufficient to make the oxygen and nutrients contained in the medium available to the cells yet gentle enough not to damage them. In the case where cells are grown in suspension the medium must also circulate at a rate sufficient to maintain the cells in suspension. By use of the sparger of the present invention gas is introduced to a liquid medium in the form of small bubbles of a controlled size to produce a gentle circulation of the medium and where applicable to maintain the cells in suspension without damage.

Most fermenter-style cell culturing apparatus are elaborate and expensive to manufacture. The present invention provides a simple and inexpensive apparatus for the cultivation of cells, especially eukaryotic cells. For some applications, the cell culture vessel, of the present invention is made from plastics and provided to the user as a disposable, sterilized unit complete with sparger.

BRIEF DESCRIPTION OF THE DRAWINGS

A further understanding of the invention may be had by referring to the accompanying drawings, wherein.

DETAILED DESCRIPTION OF THE INVENTION

Figures 1, 2:
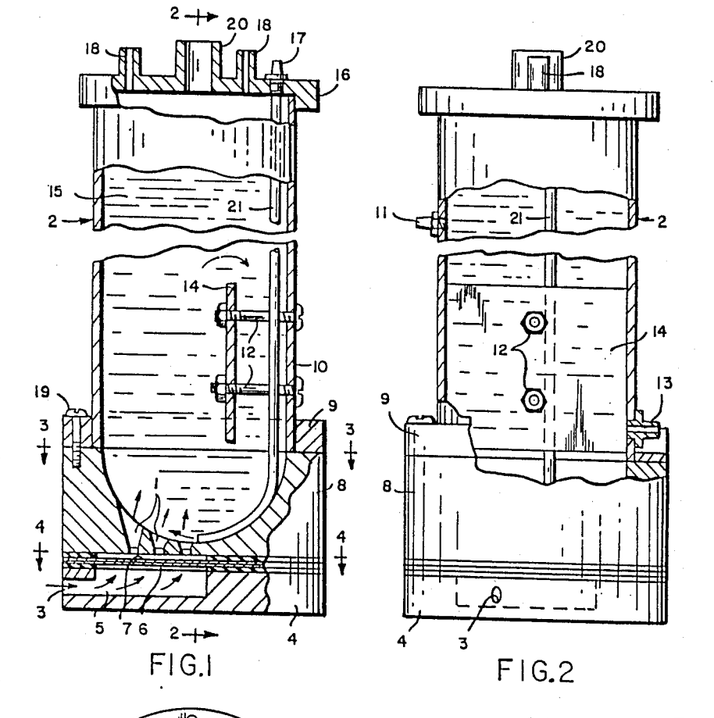
FIG. 1 shows a front elevation view with parts broken away of a preferred embodiment of a sparger and cell culture apparatus in accordance with the present invention.
FIG. 2 shows a side elevation view of FIG. 1.
Figure 8:
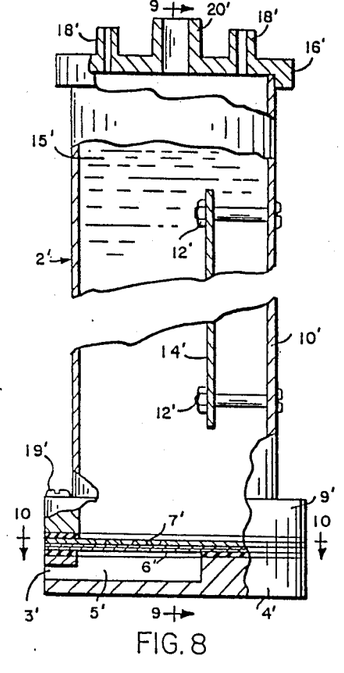
FIG. 8 shows a front elevation view with parts broken away of a second embodiment of a sparger and cell culture apparatus of the present invention.
Figure 9:
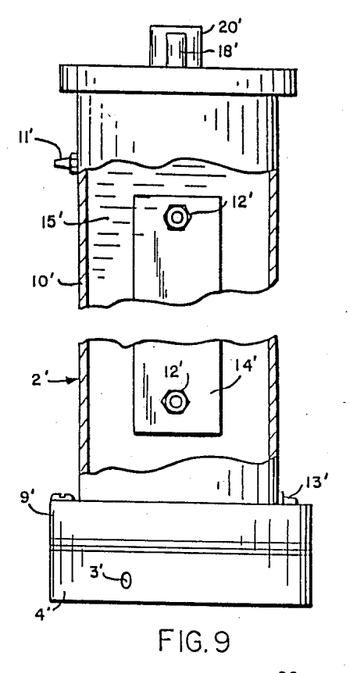
FIG. 9 shows a side elevation view of FIG. 8.

Referring to the drawings, FIGS. 1 and 2 illustrates an apparatus for cultivating cells, comprising a cylindrical tube 2 having walls 10 for containing a liquid medium 15 and provided with inlet means 11 and outlet means 13 for the liquid medium; a sparger comprising a gas inlet means 4, a first gas permeable member 6, the first member being substantially water impervious, i.e., it does not pass liquid water under normal operating conditions, preferably, it is made from a hydrophobic material; a second gas permeable member 7, a gas distribution means 8; a ring support 9 for the tube 2; a baffle means 14; support means for the baffle means 12; wall of the tube 10; a cover 16 for enclosing the tube provided with a sampling port 20, vents 18, gas inlet means 17 and gas distribution means 21. FIGS. 8 and 9 show another preferred embodiment of the present invention. Similar structures are identified by the same numeral followed by a "prime".

Gas enters the apparatus through the gas inlet means 3, passes into the gas chamber 5, through the first and second gas permeable members 6 and 7, exits through the gas distribution means 8 and enters the liquid medium 15 contained in the tube 2. The gas enters the tube 2 in the form of bubbles, formed as the gas passes through the pores in the gas permeable members 6 and 7 and the openings 1 in the gas distribution means 8. The first substantially water-impervious member 6 prevents the liquid medium 15 from passing through it into the gas chamber 5 positioned below.

A gas pressure of up to 100 psig is used under normal operating conditions. The pressure selected depends upon a number of variables including type of cell being cultured, desired rate of circulation, size and configuration of the cell culture apparatus, volume and contents of the liquid medium, filter specifications and configuration of the sparger.

Figure 13:
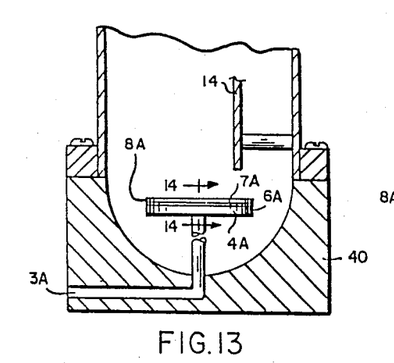
FIG. 13 shows a partial front elevation view of a third embodiment of a sparger and cell culture apparatus according to the present invention.

Formation of the bubbles is effected by the nature of the material that makes up the gas permeable members 6 and 7 and the structure and arrangement of the openings 1 in the gas distribution means 8. The configuration of the gas inlet means 4 will depend in part upon the location of the sparger relative to the culture vessel. In some embodiments the gas inlet means 4 also comprises the bottom of the tube 2. The bottom of the tube 2 is flat or in preferred embodiments arcuately concave. In embodiments where the gas inlet means 4 comprises the bottom of the tube, it must be sufficiently thick to support the tube 2 as well as to allow for an inlet passage 3 for supplying gas to gas chamber 5. In some embodiments, the gas inlet means 8 is incorporated in the bottom of the tube, e.g., a possible construction when the cell culture apparatus and sparger are made from plastic which can be injected molded as discussed below. In other embodiments, the sparger will be located within the vessel in a lower portion thereof as shown in FIG. 13.

Figure 6:
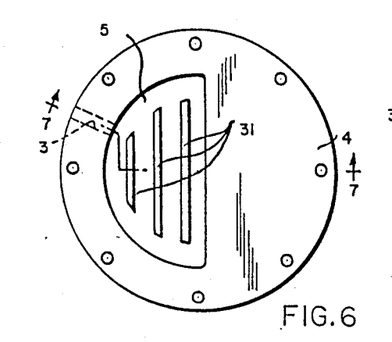
FIG. 6 shows a plan view of an embodiment of a a gas inlet means in accordance with the present invention.
Figure 7:
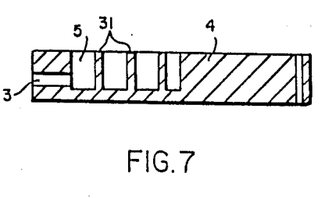
FIG. 7 shows a section taken along line 7—7 in FIG. 6.
Figure 14:
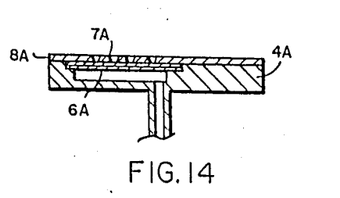
FIG. 14 shows a section taken along line 14—14 of FIG. 13.

In preferred embodiments the gas inlet means 4 provides support for the first and second gas-permeable members 6 and 7 as well as for the gas distribution means 8. In the embodiment shown in FIGS. 1 and 6 the gas inlet means 4 provides a bottom for the tube 2 and support for the gas permeable members 6 and 7. As shown in FIGS. 13 and 14 the gas inlet means 4A does not provide a bottom for the tube 2 but does provide support for the first and second gas permeable members 6A and 7A.

In FIG. 1 the gas inlet means 4 comprises a nonporous member provided with a passageway 3 opening into a gas chamber 5 for conducting gas into the gas chamber 5, the top of the gas chamber 5 opens adjacent the gas permeable member 6 so as to allow gas to pass from the chamber 5 through the gas permeable members 6 and 7 and the gas distribution means 8. The gas chamber 5 is provided with support members for the gas permeable members 6 and 7 comprising spaced parallel plates 31 extending from the bottom of the gas chamber 5 to the top thereof, adjacent the first gas permeable member 6.

Figure 3:
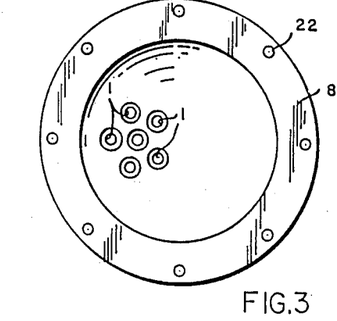
FIG. 3 shows the gas distribution means of FIG. 1 as section taken along line 3—3 in FIG. 1.
Figures 4, 5:
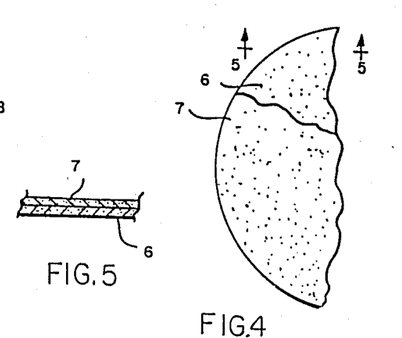
FIG. 4 shows a plan view of two gas permeable members according to an embodiment of the present invention.
FIG. 5 shows a section taken along line 5—5 in FIG. 4.
Figures 10, 11, 12:
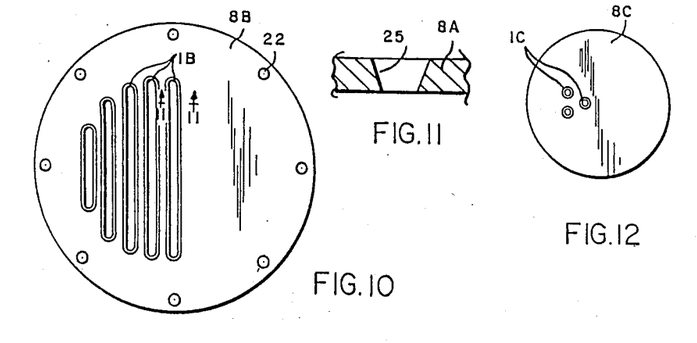
FIG. 10 shows a plan view of a second embodiment of the gas distribution means.
FIG. 11 shows a section taken along line 11—11 of FIG. 10.
FIG. 12 shows a plan view of a third embodiment of the gas distribution means.

The dimensions, shape, number and positioning of the openings 1 in the gas distribution means 8 depend in part upon the configuration of the cell culture vessel used and the desired bubble size and rate of circulation of the liquid. Desired bubble size and rate of circulation will be determined by the nature and form of the cells being cultured, e.g., cells grown in suspension may require a gentler rate of circulation that cells that are grown encapsulated, or in a micro carrier. The openings are arranged in a manner to produce uniform bubbling and to allow for optimum circulation of the liquid medium by means of the rising form of the bubbles. The openings may be selected from a variety of shapes, including slots and circles. Alternative embodiments of the gas distribution means 8, are shown in FIGS. 3, 10 and 12. The openings 1 in the gas distribution means 8 shown in FIG. 3 are constructed in such a way to allow for optimum bubble formation where the openings therein contact the second gas permeable member 7. In another preferred embodiment, shown in FIGS. 10 and 11, the sides 25 of the openings 18 are beveled or vee-shaped in order to inhibit bubbles from coalescing along the sides 25 as they are released from the bottom of the vee-shaped opening, adjacent the second gas permeable member 7, and enter into and rise in the liquid.

In preferred embodiments of the present invention two gas permeable members are present. The first gas permeable member 6 is substantially water-impervious in the direction of the gas chamber 5 and prevents the flow of liquid into the gas chamber 5 under normal operating conditions. Suitable materials for the first gas permeable member 6 include Teflon, polypropylene or polyethylene filters. As used herein "filters" shall include membranes, screen filters and membrane filters. A particularly preferred material is hydrophobic Teflon. Suitable materials for the second gas-permeable member include polyester, nitrocellulose, cellulose acetate and nylon filters. Particularly preferred materials are hydrophilic polyesters. The pore size of the filters is selected so as to, in concert with the openings 1 in the gas distribution means 8, form the gas into bubbles. The pore size of the first gas permeable member 6 is 0.02 to 1.0 micrometers, more preferably 0.02 to 0.2 micrometers. In some embodiments, the pore size of the first gas permeable member 6 may be selected so as to sterilize the gas entering the system. If it is desired to sterilize the gas entering the sparger the first gas permeable member 6 is selected to have a pore size ranging from 0.02 to 0.22 micrometers. The pore size of the second gas permeable member 7 is 0.22 to 100.0 micrometers, more preferably 0.5 to 5 micrometers.

In embodiments wherein only one gas permeable member is present, it is preferred that said member be substantially water-impervious in the direction of the gas chamber. Suitable materials include Teflon, polypropylene or polyethylene filters. If said gas permeable member is selected from materials such as polyester, nitrocellulose, cellulose acetate or nylon filters, gas is introduced through the gas passage into the gas chamber at a pressure sufficient to prevent backflow of liquid into the gas chamber during operation of the cell culture apparatus.

The culture vessel may be of any shape which will accommodate one or more baffle means 14 to direct the circulation of the medium imparted by the gas. In a preferred embodiment shown in FIGS. 1 and 2 the vessel comprises an upright cylindrical tube 2 provided with top member 16 and a bottom member comprising the gas inlet means 3, first and second gas permeable members 6 and 7 and gas distribution means 8, all of which are in this embodiment connected to the tube in a removable manner by means of screws 19 and 22 (shown in FIG. 3). FIGS. 1 and 2 show an embodiment for continuous culture wherein the tube 2 is provided with an inlet means 11 and an outlet means 13 for the medium. The top member 16 is provided with one or more vents 18 and one or more sampling ports 20. In the embodiment shown in FIGS. 1 and 2 the top member is also provided with a hose barb 17 for connection to a supply of gas and a tube 21 connected to the top 16 immediately below the hose barb 17 and extending to the bottom of the culture vessel so as to deliver gas to the bottom thereof. The gas so delivered is used to resuspend any material which settles from the liquid medium. In another embodiment shown in FIG. 13, the bottom of the tube is formed by a solid member 40 being provided with a gas inlet means 4A.

Figure 15:
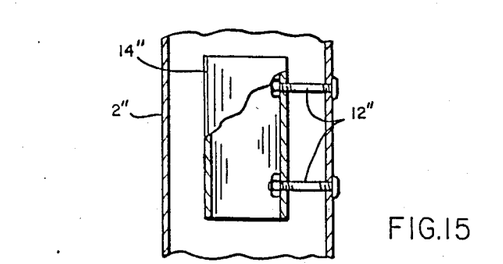
FIG. 15 shows a third embodiment of a baffle means in accordance with the present invention.

As shown in the Figures, a baffle 14 is positioned in the culture vessel so as to define two regions, preferably one larger than the other. The baffle 14 is positioned in the vessel with respect to the sparger so as to direct the circulation of the medium imparted by the gas introduced by the sparger. In a preferred embodiment shown in FIG. 1, the baffle 14 is a rectangular plate extending axially in said vessel from a lower to an upper region thereof, extending laterally to contact the inner wall 10 of the vessel, spaced from the top and bottom of the vessel, and supported by means of a support member 12, one end of which is attached to the inner wall 10 of the tube 2 and the other end to the baffle means 14. In another embodiment shown in FIGS. 8 and 9, the baffle means 14' is spaced from the inner wall of the tube 2'. In yet another preferred embodiment shown in FIG. 15, the baffle means is an open cylindrical tube extending in said vessel upwardly from a lower region thereof and spaced from the inner wall of and the top and bottom members of the vessel.

The tube 2 and its top and bottom members may be selected from a variety of materials that are non-toxic and sterilizable. In preferred embodiment the material will be a plastic selected from the group polystyrene, polycarbonate and polysulfone. In a particularly preferred embodiment the material of choice will be a plastic such polystyrene which can be injection molded.

The present invention also provides a method, embodying the sparger and cell culture apparatus disclosed herein, of cultivating cells in a liquid medium which comprises the steps of introducing gas into a gas inlet means; passing the gas from the gas inlet means through a first and second gas permeable member; distributing the gas passing from the second gas permeable member through a gas distribution means into a region of the vessel defined by a baffle means so that the gas rises in the region into which it is introduced and falls in another region defined by the baffle means; and continuously circulating the medium thereby.

The liquid medium selected will depend upon the environmental and nutritional requirements of the cells being cultured. In a preferred embodiment, the cells cultured are hybridoma cells and the medum selected is a defined, serum free medium.

Thus we have described and provided examples of a unique sparger for introducing gas to a liquid medium and methods of and apparatus for culturing cells. Although the sparger and methods and apparatus of the present invention have been described in terms of cell culture, it should be understood the same may be used in any process whereby gas is injected into a liquid.

This invention will be further understood with reference to the following examples which are purely exemplary in nature and are not meant to be utilized to limit the scope of the invention.

EXAMPLES

The conditions set forth below were used in Examples 1 through 4. The experiments were carried out under sterile conditions at 37° C. Cells from HB-12, a hybridoma cell line developed at Ventrex, were seeded at approximately $1 \times 10^5$ cells/ml in HL-1 medium with 2% fetal bovine serum (FBS) and antifoam B (Dow Corning) at a dilution of 1: 15,000. HL-1 is a defined, serum-free medium commercially available from Ventrex especially designed for the growth of hybridomas. HL-1 was used in these examples because of its low protein content and high buffering capacity. However, DMEM [(Dulbecco's modified Eagle's medium F-12 (Ham)] could also be used in these experiments. Glutamine (Gibco) was added to give a final concentration of 2 mM and gentamycin (Gibco) was added to give a final concentration of 50 mcg/ml. A T75 flask received 20 ml of cell culture and the cell culture apparatus of the present invention (hereinafter sometimes referred to as "CELLIFT" a trademark of Ventrex.) received 500 ml. Cell viability was determined using the standard trypan blue exclusion method. In Examples 1, 2 and 3 the batch processing method of cell culture was used. In Example 4 a constant flow, steady state method was used.

EXAMPLE 1 HYBRIDOMA VIABILITY

Cell culture carried out in a cell culture apparatus according to the present invention, having the configuration shown in FIGS. 8 and 9 and the gas distribution means shown in FIGS. 8, 9 and 12, was compared with cell culture carried out in a standard T75 flask. The first gas permeable member used was a 0.02 micrometer Teflon membrane (Millipore) which also served to sterilize the gas entering the system. The second gas permeable member used was a 1 micron polyester screen filter (Tetko).

TABLE I

| % VIABILITY HYBRIDOMA HB 12 | | |
| --- | --- | --- |
| DAY | CELLIFT* | T 75 FLASK+ |
| 1 | 91% | 80% |
| 4 | 91% | 80% |
| 5 | 59% | 66% |
| 7 | 42% | 28% |

*500 ml HL—1 + 2% FBS
+20 ml HL—1 + 2% FBS
Concentration of cells equal in both flasks at initiation of experiment.

EXAMPLE 2 ANTIBODY PRODUCTION

The same conditions as in Example 1, except that total antibody synthesis was measured using a standard ELISA procedure. HB12 secrets IgG.

TABLE II

| ANTIBODY PRODUCTION WITH HYBRIDOMA HB 12 | | |
| --- | --- | --- |
| DAY | CELLIFT* | T 75 FLASK+ |
| 1 | 5.9 mg | 0.9 mg |
| 4 | 62.9 mg | 4.8 mg |
| 5 | 81.6 mg | 13.52 mg |
| 7 | 108.0 mg | 12.50 mg |

*As in Table I
+As in Table I

EXAMPLE 3 TOTAL ANTIBODY LEVELS MEASURED BY A STANDARD ELISA PROCEDURE

Conditions as in Example 1, except that antibody production is normalized against cell number giving an indication of yield of antibody per cell mass. This table indicates a higher yield in the apparatus of the present invention than the T75 flask.

TABLE III

| ANTIBODY CONCENTRATION IN MICROGRAMS PER $10^6$ CELLS PER ML (HB 12) IN BATCH CULTURE | | |
| --- | --- | --- |
| DAY | CELLIFT* | T 75 FLASK+ |
| 1 | 107.3 | 66.4 |
| 4 | 229.1 | 116.1 |
| 5 | 171.2 | 191.8 |
| 7 | 360.0 | 241.3 |

*As in Table I
+As in Table I

EXAMPLE 4

Cell culturing carried out in an apparatus according to the present invention, having the configuration show in FIGS. 1 and 2 (except that hose barb 17 and gas inlet 21 were not used) and the gas distribution means shown in FIG. 3, was compared with cell culture carried out in a T75 flask. Otherwise conditions were as in Example 1, except that a continuous feeding of the culture in the cell culture apparatus was initiated on day 7 with an infusion of approximately 3.6 liters by day 14. Total antibody was determined for accumulated fluids.

TABLE IV

| ANTIBODY YIELD IN MG IN CONTINUOUS CULTURE VS STATIONARY CULTURE IN A T 75 FLASK WITH HYBRIDOMA HB 12. | | |
| --- | --- | --- |
| DAY | CELLIFT* | −T 75 FLASK+ |
| 8 | 175 mg | 11.7 mg |
| 14 | 325 mg | 11.2 mg |

*HL—1 Medium + 2% FBS at an exchange rate of approx. 0.35 ml per minute beggining on day 7. Approximately 3.6 liters of medium were exchanged in this study
+HL—1 medium + 2% FBS with no exchange of medium.
1. pH shifts in Cellift were effectively controlled using a well buffered medium (HL—1, Ventrex).
2. Foaming is minimal in medium containing 2% FBS, and was reduced by using HL—1 and an antifoam agent (Antifoam B, Dow Corning).

Although the sparger and methods and apparatus of the present invention have been described in terms of cell culture, it should be understood the same may be used in any process whereby gas is injected into a liquid. Additional advantages and modifications of the invention disclosed herein will occur to those person skilled in the art. Accordingly, the invention in its broader aspects is not limited to the specific details or illustrated examples described herein. Therefore, all departures made from the detail are deemed to be within the scope of the invention as defined by the appended claims.

What is claimed is:

1. A device for introducing gas into a liquid contained in a vessel so disposed as to introduce gas therethrough comprising: a gas inlet means; at least one gas permeable filter disposed adjacent the gas inlet means, the gas permeable filter being substantially impervious to the liquid; and a gas distribution means disposed adjacent the gas permeable filter; the gas inlet means, the gas permeable filter and the gas distribution means being sealably connected.

2. A device according to claim 1 wherein the gas distribution means comprises: a nonporous filter provided with at least one opening so disposed as to direct the gas into the vessel.

3. A device according to claim 2 wherein the opening is elongate.

4. A device according to claim 3 wherein in cross-section the elongate opening is vee-shaped, the point of the vee being adjacent the gas permeable filter.

5. A device according to claim 2 wherein the opening is arcuately concave, the bottom of the opening adjacent the gas permeable filter being provided with a center opening.

6. A device according to claim 2 wherein the opening is spherically concave, the bottom of the opening adjacent the gas permeable filter being provided with a center opening.

7. A device according to claim 1 wherein said gas inlet means comprises: a nonporous member provided with a passageway opening into a gas chamber for conducting gas into the gas chamber, the gas chamber being provided with an opening adjacent the gas permeable filter so located as to allow gas to pass from the gas chamber through the gas permeable filter.

8. A device according to claim 7 wherein the opening is concave.

9. A device according to claim 7 wherein the opening comprises: a support means for the gas permeable filter.

10. A device according to claim 7 wherein the gas chamber is provided with a support means for supporting the gas permeable filter, the support means comprising: spaced parallel bars extending the length and height of the opening and connected to the sides thereof.

11. A device according to claim 1 wherein said filter is substantially water-impervious.

12. A device according to claim 1 wherein said substantially water-impervious filter is Teflon, polypropylene or polyethylene.

13. A device for introducing gas into a liquid contained in a vessel so disposed as to introduce gas therethrough comprising: a gas inlet means, a first gas permeable filter disposed adjacent the gas inlet means, the first gas permeable filter being substantially impervious to the liquid; a second gas permeable filter; and a gas distribution means disposed adjacent the gas permeable filter; the gas inlet means, the first and second gas permeable filters and the gas distribution means being sealably connected.

14. A device according to claim 13 wherein the second gas permeable filter is hydrophilic.

15. A device according to claim 14 wherein the hydrophilic filter is polyester, nitrocellulose, cellulose acetate or nylon.

16. An apparatus for cultivating living cells in a liquid medium comprising: a vessel for the liquid medium; at least one baffle means supported within the vessel and spaced from the top and bottom thereof, the baffle means defining at least two regions; said apparatus having sparger means for introducing gas into a liquid contained in a vessel, said sparger means being so disposed as to introduce gas therethrough into a region defined by the baffle means, the sparger means comprising: a gas inlet means; at least one gas permeable filter disposed adjacent the gas inlet means, the first gas permeable filter being substantially impervious to the liquid; and a gas distribution means disposed adjacent the gas permeable filter; the gas inlet means, the gas permeable filter and the gas distribution means being sealably connected.

17. An apparatus according to claim 16 wherein the baffle means comprises a plate.

18. An apparatus according to claim 16 wherein the plate is disposed axially within the vessel and spaced from the walls thereof.

19. An apparatus according to claim 16 wherein said baffle means comprises a cylindrical tube.

20. An apparatus according to claim 16 wherein said cylindrical tube is disposed axially in the vessel and spaced from the walls thereof.

21. An apparatus according to claim 16 wherein the vessel is provided with means for introducing gas into the bottom of the vessel to effect dispersion of cells and other material which may settle out of the liquid medium.

22. An apparatus according to claim 16 wherein the vessel is provided with inlet and outlet means for the liquid medium.

23. An apparatus according to claim 16 wherein the cells are euokaryotic.

24. An apparatus according to claim 16 wherein the cells are mammalian.

25. An apparatus according to claim 16 wherein the cells are hybridomas.

26. An apparatus according to claim 16 wherein the cells are plant cells.

27. An apparatus according to claim 16 wherein the liquid medium is a defined, serum free medium.

28. An apparatus for cultivating living cells in a liquid medium comprising: a vessel for the liquid medium; at least one baffle means supported within the vessel and spaced from the top and bottom thereof, the baffle means defining at least two regions; said apparatus having sparger means for introducing gas into a liquid contained in a vessel, said sparger means being so disposed as to introduce gas therethrough into a region defined by the baffle means, the sparger means comprising: a gas inlet means; a first gas permeable filter disposed adjacent the gas inlet means, the first gas permeable filter being substantially impervious to the liquid: a second gas permeable filter disposed adjacent the first gas permeable filter; and a gas distribution means disposed adjacent the second gas permeable filter; the gas inlet means, the gas permeable filters and the gas distribution means being sealably connected.

29. A method of introducing gas into a liquid without adverse affect on sensitive biological materials contained therein which comprises the steps of introducing gas into a gas inlet means; passing the gas from the gas inlet means through a first and second gas permeable filter, the first gas permeable filter being substantially impervious to the liquid; and distributing the gas passing from the second gas permeable filter through a gas distribution means into a liquid medium.

30. A method of cultivating cells in a liquid medium contained in a vessel which comprises the steps of introducing gas into a gas inlet means; passing the gas from the gas inlet means through a first and second gas permeable filter the first gas permeable filter being substantially impervious to the liquid; distributing the gas passing from the second gas permeable filter through a gas distribution means into a zone of the vessel defined by a baffle means so that the gas rises in the zone into which it is introduced and falls in another zone defined by the baffle means; and continuously circulating the medium thereby.

31. A method according to claim 30 wherein the circulating step has no adverse effect upon cells around and over which the liquid medium circulates.

32. A method according to claim 30, wherein the circulating step has no adverse effect upon of cells contained in the liquid medium and circulated therewith.

33. A method according to claim 30 wherein the cells are mammalian cells.

34. A method according to claim 30 wherein the cells are hybridoma cells.

35. The method of cultivating living cells with the aid of an apparatus for cultivating living cells in a liquid medium comprising: a vessel for the liquid medium; at least one baffle means supported within the vessel and spaced from the top and bottom thereof, the baffle means defining at least two regions; said apparatus having sparger means for introducing gas into a liquid contained in a vessel, said sparger means being so disposed as to introduce gas therethrough into a region defined by the baffle means, the sparger means comprising: a gas inlet means; at least one gas permeable filter disposed adjacent the gas inlet means, the gas permeable filter being substantially impervious to the liquid; and a gas distribution means disposed adjacent the gas permeable filter; the gas inlet means, the gas permeable filter and the gas distribution means being sealably connected; the method comprising the steps of introducing gas into the gas inlet means; passing the gas from the gas inlet means through the gas permeable filter; distributing the gas passing from the gas permeable filter through the gas distribution means into the region of the vessel defined by the baffle means so that the gas rises in the region into which it is introduced and falls in another region defined by the baffle means and continuously circulating the medium thereby.

* * * * *

UNITED STATES PATENT AND TRADEMARK OFFICE
CERTIFICATE OF CORRECTION

PATENT NO. : 4,668,632

DATED : May 26, 1987

INVENTOR(S) : Michael W. Young, Henry W. Founds, Peter Zuk, Jr.

It is certified that error appears in the above-identified patent and that said Letters Patent is hereby corrected as shown below:

At column 6, line 64, replace "18" with --1B --.

Signed and Sealed this

Twelfth Day of January, 1988

*Attest:*

DONALD J. QUIGG

*Attesting Officer*  *Commissioner of Patents and Trademarks*